United States Patent
Maue et al.

(10) Patent No.: US 6,761,590 B2
(45) Date of Patent: Jul. 13, 2004

(54) SMALL-DIMENSIONED COUPLER PLUG, ESPECIALLY FOR A PLANAR BROADBAND LAMBDA PROBE

(75) Inventors: Hans-Heinrich Maue, Bietigheim-Bissingen (DE); Wolfgang Pade, Illingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/182,877
(22) PCT Filed: Nov. 23, 2001
(86) PCT No.: PCT/DE01/04413
§ 371 (c)(1), (2), (4) Date: Nov. 11, 2002
(87) PCT Pub. No.: WO02/45212
PCT Pub. Date: Jun. 6, 2002

(65) Prior Publication Data
US 2003/0119381 A1 Jun. 26, 2003

(30) Foreign Application Priority Data
Dec. 1, 2000 (DE) ...................................... 200 20 376 U

(51) Int. Cl.[7] .............................................. H01R 13/66
(52) U.S. Cl. ...................................... 439/620; 439/913
(58) Field of Search ................................ 439/620, 752, 439/913

(56) References Cited

U.S. PATENT DOCUMENTS

| | | | |
|---|---|---|---|
| 5,947,775 A | 9/1999 | Yamamoto et al. | 439/752 |
| 6,132,256 A | 10/2000 | Morsdorf et al. | 439/620 |
| 6,554,649 B2 * | 4/2003 | Pade | 439/620 |

* cited by examiner

*Primary Examiner*—Renee Luebke
*Assistant Examiner*—Ann McCamey
(74) *Attorney, Agent, or Firm*—Kenyon & Kenyon

(57) ABSTRACT

A small and compact coupler plug for a planar broadband lambda probe includes a housing having a basic body and a cover element as well as electrical components, which can be inserted into the housing and fixed in place, as well as an adjustment unit for a probe, in particular a planar broadband lambda probe, the adjustment unit being arranged within the coupler plug or outside the coupler plug via a further contact element. The cover element can be mounted over the balancing unit, and primary and secondary locking devices that cooperates with the cover element may be provided, the secondary locking device being configured as a fixing element to fix in place at least one electrical contact that is inserted in the housing, and this fixing element also having support elements that point to the cover element, such that the cover element closes in the end position of the secondary element.

12 Claims, 3 Drawing Sheets

SMALL-DIMENSIONED COUPLER PLUG, ESPECIALLY FOR A PLANAR BROADBAND LAMBDA PROBE

FIELD OF THE INVENTION

The present invention relates to a coupler plug connector, in particular, for a plug connector for a planar lambda probe.

BACKGROUND INFORMATION

Coupler plugs are used for the connection between a cable harness plug and a lambda probe. The terminals provided in the coupler plug are used for the adjustment, the signal, and/or the heating of the probe. Currently, lambda probes in combination with lambda regulation and 3-way catalytic converters, are used for exhaust-gas purification. The lambda probe, which can be screwed into, for example, an exhaust gas system, includes a sensor for ascertaining the oxygen content in the exhaust gas.

The residual oxygen content is very well suited as a measuring variable and regulates the air-fuel ratio, because the latter indicates precisely whether the air-fuel mixture is burning completely.

In this context, the lambda probe generates a voltage signal, which represents the instantaneous value of the mixture composition, and which follows the mixture changes. The fuel supply to the engine is regulated by a carboration system in accordance with the signal from the lambda probe such that a stoichiometric air-fuel ratio $\lambda=1$ is achieved. In accordance with the design of the exhaust gas system and with the conditions for use, heated or unheated probes are used. The lambda probe has other uses apart from motor vehicles, e.g., for regulating gas motors or oil/gas burners.

In particular, broadband lambda probes have a modular design and, in conjunction with planar techniques, can be integrated in a plurality of functions. They typically have functional layers, which are made up of a porous protective layer, an external electrode, a sensor foil, an internal electrode, a reference air channel foil, an insulation layer, a heating element, a heating foil, a resistor or an adjustment element, and terminal contacts.

Because the broadband lambda probe is made up of the combination of a Nernst concentration cell (sensor cell) and a pump cell that transports oxygen ions, it is able to carry out very precise measurements not only in the stoichiometric point at $\lambda=1$, but also in the lean and rich range.

Every probe is individually adjusted for a balancing effect. For this purpose, the probe has a built-in resistor ("mini-hybrid"). The adjustment may be accomplished by ablating the resistor layer that is situated on a ceramic substrate using a laser beam, thus generating a change in the resistance and resulting in a balancing.

In a given embodiment, the adjustment unit, or the resistor, may be arranged on the probe. In an alternative exemplary embodiment, the resistor is arranged outside, for example, on a cable harness plug that is coupled to the probe.

Heretofore, the balancing has been carried out by transporting the housing of the coupler plug to the balancing position without the cover element, the resistor being installed in the coupler plug. According to this technique, after the appropriate laser treatment for the balancing, the cover element is then subsequently mounted at a different assembly position.

To prevent humidity, contamination, or the like from penetrating into the coupler plug, and to assure that the appropriate atmosphere is present within the coupler plug, the cover element has additional seals. In addition, pressure compensating elements are arranged on the housing of the coupler plug.

One disadvantage of this design is that additional working and assembly steps are necessary after the balancing to close up the coupler plug in a functionally correct manner.

In addition, it is necessary to separately manufacture a supplemental cover element along with a seal, and to make this cover element available in the balancing area.

SUMMARY

An object of the present invention is to provide a coupler plug for a planar broadband lambda probe that can be produced in a cost-effective manner and have very small dimensions.

This object may be achieved by providing a coupler plug that includes a cover element that can be mounted over the adjustment element, and that has primary and secondary locking device that cooperates with the cover element, the secondary locking device being provided as a fixing element to fix in place at least one electrical contact that is installed in the housing. The fixing element also has support elements that point to the cover element, such that the cover element only completely closes in the end position of the secondary element (the fixing in place of the electrical contact).

According to an example embodiment of the present invention, the coupler plug is configured so as to be of small dimensions, because, due to the compact installation of electrical contacts in a basic body and the arrangement of the adjustment element likewise in the coupler plug, the external dimensions of the coupler plug, which may be arranged between a cable harness and a lambda probe, are very small.

In addition, according to an exemplary embodiment, the coupler plug according to the present invention may include only a small number of parts. As a result, a cost-effective and efficient manufacturing process can be implemented.

Because the basic body may be completely surrounded by the cover element, it is possible to seal off the interior of the coupler plug through an arrangement of sealing lips within the cover element, or an arrangement of seals in the basic body, so that the coupler plug is protected, particularly from spray water and/or soiling.

This also aids in the latching of the cover element to the basic body. According to an embodiment of the present invention, a first and second latching device, or a primary and a secondary locking device, are provided. The latter may be configured such that the cover element has latching arms, which, in the closed state of the cover, are in contact with the basic body of the coupler plug and bring about a coupling there using latching hooks.

According to a further embodiment, the primary locking device operates in two stages. In a first stage, the cover element latches such that it is held on the basic body. As a result of continued pressure of the cover element in the direction of the basic body, the fixing element embedded in the basic body may be fixed onto the electrical contact element running in the basic body, for example, a planar plug sleeve, which is connected to the lambda probe. However, the fixing only takes place by the fixing element being pressed onto the contact element, so that the contact element and the fixing element have a secure connection. In addition, the fixing element may be restrained in the basic body, which means that, in the mounted state of the contact element, the fixing element moves only in the axial push-on direction of the cover. In addition, support elements may be provided on the fixing element, pointing away from the fixing element, the support elements extending in the direction of the cover element.

In the non-actuated state of the secondary locking device, i.e., the non-fixing of the contact element, the support elements may extend far beyond the basic body of the coupler plug such that the cover element is held only by the first latching action of the primary locking device. In response to a complete activation and thus the proper fixing in place of the contact element, the cover element undergoes the second latching action of the primary locking device.

This has the advantage that it is possible in a simple manner to check whether a successful contacting and therefore securing of the electrical contact element has been achieved with respect to the lambda probe, and that the cover element is tightly closed with respect to the basic body.

Advantageously, hanging devices may be provided on the periphery of the cover element which make it possible to secure the coupler plug on another part, for example, using a groove-and-tongue connection, or, alternatively, through hanging devices such that electrical lines can be mounted on the coupler plug.

Mounting possibilities are optionally provided for spraywater sleeves.

A further advantage of the present invention is that the aforementioned seals on the cover element can be injectionmolded, so that they are arranged in a nondetachable manner.

To assure a constant transition resistance between the adjustment unit and the electrical contact elements, a solder connection is provided.

The cover element is advantageously made of PBT (polybutylene terephthalt) or equivalent materials.

In a further advantageous exemplary embodiment of the present invention, the cover element is configured so as to be transparent. As a result, it is possible that the cover element can be mounted even before the balancing, because, if the cover elements are transparent, the balancing can be carried out through the cover element using a laser beam.

DETAILED DESCRIPTION

Figure 1:
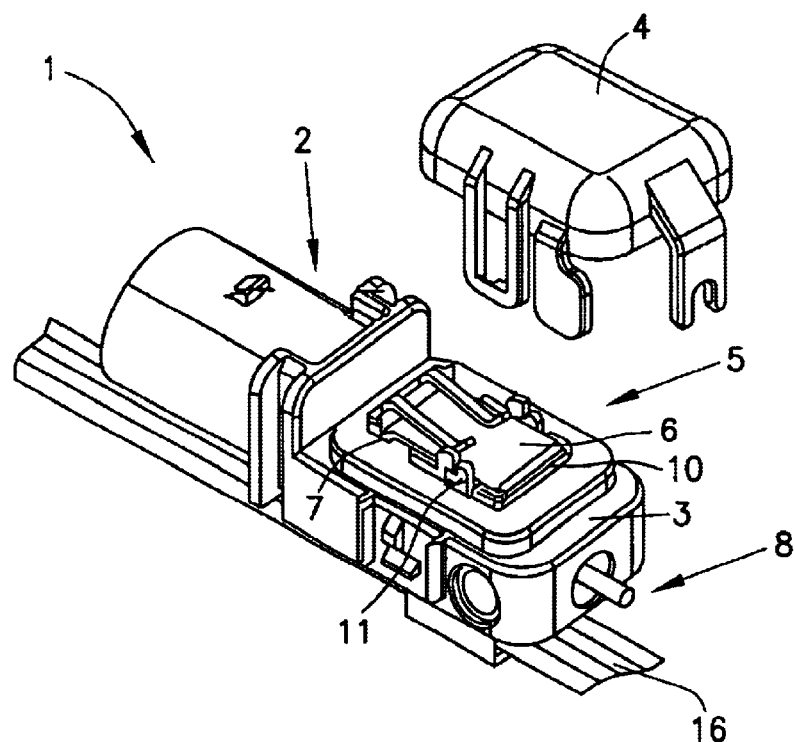
FIG. 1 depicts a perspective view of the coupler plug according to the present invention, having a detached cover element.

Coupler plug 1, depicted in FIGS. 1 through 4, includes a housing 2, which is composed of a basic body 3 and a cover element 4.

Arranged on basic body 3 in a retaining device 5 is an adjustment unit 6, which is coupled via electrical contact elements 7 to a lambda probe that connects to the coupler plug 1 via a connecting element 8.

Electrical contact elements 7 are made of metal strips that are shaped to resemble printed circuit traces, the strips on terminating on one side in coupling area 9 (shown in FIG. 4) of coupler plug 1.

Adjustment unit 6 is guided by guide elements 10, which are mainly arranged on basic body 3, and it is held in position by electrical contact elements 7.

To prevent lateral shifting of adjustment unit 6, support elements 11 are provided perpendicular to the longitudinal extension of adjustment unit 6. These support elements 11, as shown in greater detail in FIGS. 5, 6, and 7, may be configured as a part of a fixing element 12.

Fixing element 12 is provided as a secondary locking element and has the function to hold in position an electrical contact 13, which is arranged in housing 2, and which may be connected to the lambda probe.

Figure 7:
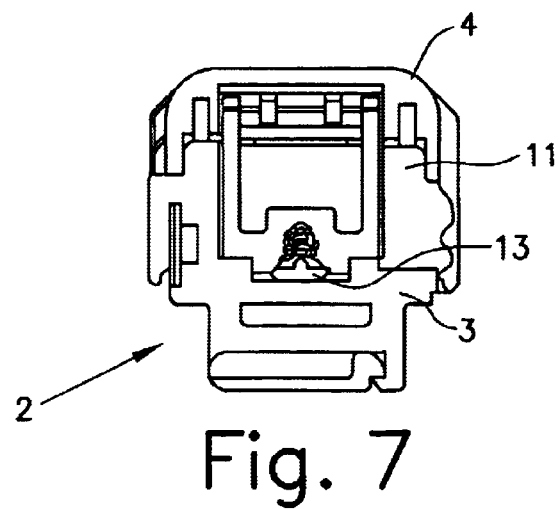
FIG. 7 depicts a cut-away view of the cable harness plug shown in FIG. 1 having the cover element in the end position.

For this purpose, fixing element 12 may be configured in its cross-section in a W shape, enclosing electrical contact 13 axially between its two arms 12a/12b, in the assembled state (shown FIG. 7).

The secondary locking element, i.e., fixing element 12, may also be configured such that it forms a single piece along with support elements 11.

Figure 5:
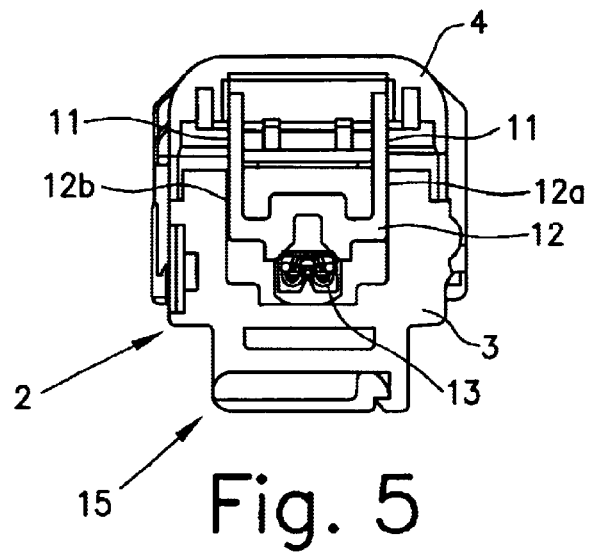
FIG. 5 depicts a cut-away view of the cable harness plug shown in FIG. 1 having the cover element in the first latching position.
Figure 6:
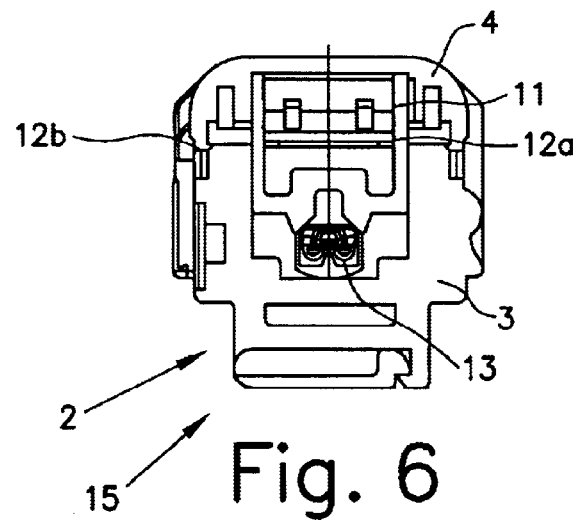
FIG. 6 depicts a cut-away view of the cable harness plug shown in FIG. 1 having the cover element immediately before the end position.

In the pre-assembled state of electrical contact 13, as is depicted in FIG. 5, support elements 11 extend far out of housing 2, so that cover element 4, which is mounted on housing 2, can be fixed only in a first latching.

The result is that, when the secondary locking device is not activated, the fixing of electrical contact 13 is not functional, and the positioning of fixing element 12 is positioned such that cover element 4 does not close (see FIG. 5).

With the correct end position, the cover element 4 adopts its own end position.

The secondary locking device, once assembled, cannot be detached after being locked without destroying coupler plug 1.

Advantageously, coupler plug 1 has on its circumference grooves 14, which make it possible to insert the coupler plug 1 into retainer supports provided for this purpose.

Figure 2:
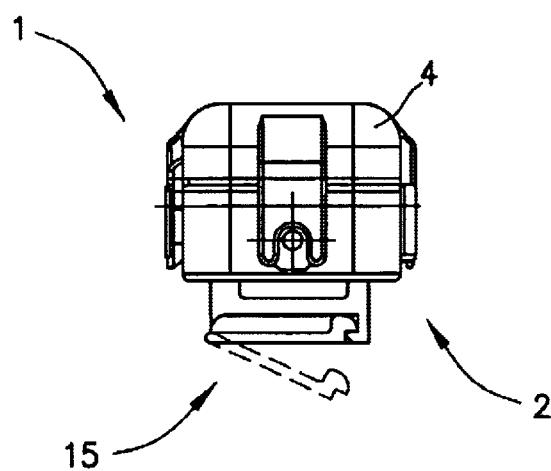
FIG. 2 depicts a rear view of the coupler plug as shown in FIG. 1.
Figure 3:
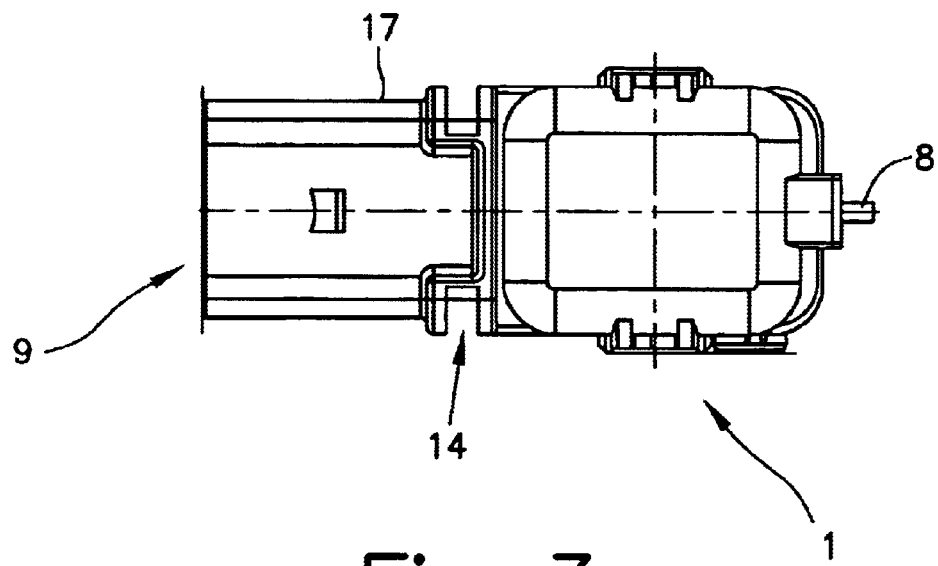
FIG. 3 depicts a top view of the coupler plug as shown FIG. 2.
Figure 4:
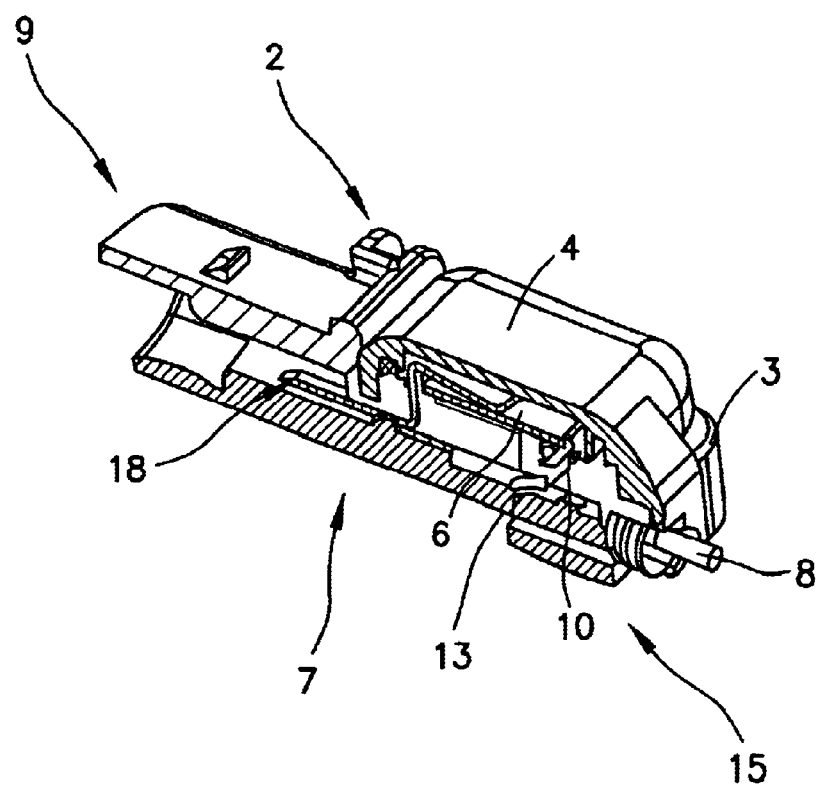
FIG. 4 depicts a perspective, cut-away view of the coupler plug shown in FIG. 1, having a cover that is mounted in place.

In addition, arranged in basic body 2 are retaining and fixing elements 16, as depicted in FIG. 2, which make it possible to arrange coupler plug 1 on electrical lines 16, as depicted in FIG. 1.

For this purpose, retaining element 15 is configured as a clip, so that coupler plug 1 can be plugged into a cable phase winding when the retaining element 13 is in the open position, and the coupler plug can then be closed as a result of a further motion.

In this way, the coupler plug can be mounted, for example, on an engine (support).

Due to its small external dimensions, it is also possible to accommodate the coupler plug in a grooved tube.

What is claimed is:

1. A coupler plug for a planar lambda probe, comprising: a housing including a basic body and a cover element;

electrical components fixably inserted into the housing;

at least one first electrical contact inserted in the housing;

an adjustment element mounted on the basic body, the covering element configured to cover the adjustment element, the adjustment element configured to adjust a planar broadband lambda probe;

a primary locking device; and a secondary locking device including a fixing element for fixing the at least one first electrical contact, and including support elements;

wherein the primary locking device and the secondary locking device each cooperate with the cover element, and the support elements of the secondary locking device extend toward the cover element such that the cover element completely closes only when the secondary locking device is in an end position.

2. The coupler plug of claim 1, further comprising:

a second contact element, the lambda probe being arranged outside the coupler plug and coupled to the coupler plug via the second contact element.

3. The coupler plug of claim 1, wherein the cover element is transparent.

4. The coupler plug of claim 1, wherein the secondary locking device is arranged between the basic body and the cover element.

5. The coupler plug of claim 1, wherein the lambda probe is arranged within the coupler plug.

6. The coupler plug of claim 5, further comprising:

third electrical contact elements including spring elements;

wherein the adjustment element is supported on the housing by the spring elements of the third electrical contact elements.

7. The coupler plug of claim 6, wherein the third electrical contact elements are electrically connected to the adjusment unit via soldered connections.

8. The coupler plug of claim 6, wherein the electrical components include plug-in contacts.

9. The coupler plug of claim 8, wherein the third electrical contact elements are electrically connected to the plug-in contacts.

10. The coupler plug of claim 9, wherein the third electrical contact elements and the plug-in contacts are integrated in a single piece.

11. The coupler plug of claim 1, further comprising:

a hanging element arranged on a periphery of the coupler plug.

12. The coupler plug of claim 11, wherein the hanging element is configured a groove for engaging a tongue element.

* * * * *